US00PP23999P2

(12) United States Plant Patent
Bergman

(10) Patent No.: US PP23,999 P2
(45) Date of Patent: Oct. 22, 2013

(54) ***CHRYSANTHEMUM* PLANT NAMED 'CIDZ0021'**

(50) Latin Name: *Chrysanthemum×morifolium*
Varietal Denomination: CIDZ0021

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 184 days.

(21) Appl. No.: 13/317,426

(22) Filed: Oct. 18, 2011

(51) Int. Cl.
*A01H 5/00* (2006.01)

(52) U.S. Cl.
USPC ..... Plt./296; Plt./286

(58) Field of Classification Search
USPC ..... Plt./286, 296
See application file for complete search history.

*Primary Examiner* — Susan McCormick Ewoldt
(74) *Attorney, Agent, or Firm* — Joshua L. Price

(57) ABSTRACT

A new *Chrysanthemum* plant named 'CIDZ0021' particularly distinguished by the small sized daisy-type inflorescences with greyed orange color, medium green foliage, very compact plant growth habit and is freely branched.

1 Drawing Sheet

Latin name of the genus and species of the plant claimed: *Chrysanthemum×morifolium.*

Varietal denomination: 'CIDZ0021'.

BACKGROUND OF THE NEW PLANT

The present invention comprises a new *Chrysanthemum*, botanically known as *Chrysanthemum×morifolium*, and hereinafter referred to by the variety name 'CIDZ0021'.

'CIDZ0021' is a product of a planned breeding program. The new cultivar has small sized daisy-type inflorescences with greyed orange color, medium green foliage, very compact plant growth habit and is freely branched.

'CIDZ0021' originated from a hybridization made in March 2004 in a controlled breeding environment in Salinas, Calif. The female parent was unknown.

The male parent of 'CIDZ0021' was a proprietary, unpatented plant identified as 'F0079' with smaller size inflorescences, smaller plant habit and faster flowering response time.

'CIDZ0021' was selected as one flowering plant within the progeny of the stated cross in the May 2005 in a controlled environment in Fort Myers, Fla.

The first act of asexual reproduction of 'CIDZ0021' was accomplished when vegetative cuttings were propagated from the initial selection in June 2005 in a controlled environment in Fort Myers, Fla.

BRIEF SUMMARY OF INVENTION

Horticultural examination of plants grown from cuttings of the plant initiated in June 2005, and continuing thereafter, has demonstrated that the combination of characteristics as herein disclosed for 'CIDZ0021' are firmly fixed and are retained through successive generations of asexual reproduction.

'CIDZ0021' has not been observed under all possible environmental conditions. The phenotype may vary significantly with variations in environment such as temperature, light intensity and day length.

Plant Breeder's Rights for this cultivar were applied for in Canada on Jul. 29, 2011, #11-7346 and in Brazil on Apr. 8, 2011, #21806.000105/2011. 'CIDZ0021' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0021' with colors being as true as possible with an illustration of this type.

The photographic drawing shows a flowering plant of the new variety, and a close-up of the flowers.

DETAILED BOTANICAL DESCRIPTION

The plant descriptions, measurements and aforementioned photographs were taken in Gilroy, Calif. in September 2011 under natural light. These plants were propagated and grown in Nipomo, Calif. and shipped to Gilroy, Calif. for the data collection and photographs. These plants were approximately 9 weeks of age, grown as 4 plants together in a 5 inch bulb pan, under greenhouse trial conditions.

Color references are made to The Royal Horticultural Society Colour Chart (R.H.S.) 2001.

TABLE 1

DIFFERENCES BETWEEN THE NEW VARIETY 'CIDZ0021' AND A SIMILAR VARIETY

| | 'CIDZ0021' | 'Yostockton' (Not patented) |
|---|---|---|
| Plant height: | Taller | Shorter |
| Inflorescence size: | Larger | Smaller |
| Flowering response time: | 7 weeks | 6 weeks |

Plant:

*Form, growth and habit.*—Herbaceous fleurette pot type, stems upright, freely branching, small foliage.

*Plant height*.—About 10.0 cm.
*Plant height* (*inflorescence included*).—14.0-15.0 cm.
*Plant width*.—15.0 cm.

Roots:
*Number of days to initiate roots*.—4 days at about 22 degrees C.
*Number of days to produce a rooted cutting*.—About 10 days at 22 degrees C.
*Type*.—Fine, fibrous, free branching.
*Color*.—RHS N155B but whiter.

Foliage:
*Arrangement*.—Alternate.
*Immature, leaf color, upper surface*.—Closest to RHS 137A but darker.
*Lower surface*.—Between RHS 137B and RHS 137C.
*Mature, leaf color, upper surface*.—Closest to RHS 137A but darker.
*Lower surface*.—Between RHS 137B and RHS 137C.
*Length*.—3.7-4.0 cm.
*Width*.—2.4-2.8 cm.
*Shape*.—Elliptical.
*Base shape*.—Attenuate.
*Apex shape*.—Mucronulate.
*Margin*.—Somewhat palmately lobed, slightly serrate.
*Texture, upper surface*.—Bifid T-shaped hairs.
*Lower surface*.—Bifid T-shaped hairs.
*Color of veins, upper surface*.—Closest to RHS 138B.
*Color of veins, lower surface*.—RHS 138B.
*Petiole color*.—RHS 138B.
*Length*.—1.3-1.6 cm.
*Diameter*.—0.2 cm.
*Texture*.—Bifid T-shaped hairs.

Stem:
*Quantity of main branches per plant*.—3-4.
*Color of stem*.—RHS 138A but appears lighter due to hairs.
*Length of stem*.—5.4-6.5 cm.
*Diameter*.—0.25-0.3 cm.
*Length of internodes*.—0.4-0.6 cm.
*Texture*.—Bifid T-shaped hairs.
*Color of peduncle*.—RHS 138A but appears lighter due to hairs.
*Length of peduncle*.—2.2-2.5 cm.
*Peduncle diameter*.—0.1-0.15 cm.
*Texture*.—Bifid T-shaped hairs.

Inflorescence:
*Type*.—Compositae type, solitary inflorescences daisy-type, borne terminally above foliage, ray florets arranged acropetally on a capitulum.
*Quantity of short days to flowering* (*response time*).—7 weeks.
*Quantity of inflorescences per plant*.—26-40.
*Lastingness of individual blooms on the plant*.—About 4 weeks.
*Fragrance*.—Slightly spicy.

Bud (just when opening/showing color):
*Color*.—RHS 178A to RHS 178B on upper side of petal; and RHS 175B to RHS 175C on the lower side with RHS 178B at the apex.
*Length*.—0.4-0.5 cm.
*Width*.—0.7 cm.
*Shape*.—Oblate.

Immature inflorescence:
*Diameter*.—1.0-2.9 cm.
*Color of ray florets, upper surface*.—RHS 160A ground color heavily overlaid and mottled with RHS 175B to RHS 175C with RHS 178A margins.
*Lower surface*.—RHS 160A ground color lightly overlaid and mottled with a muted hue of RHS 175B to RHS 175C with darker margins.

Mature inflorescence:
*Diameter*.—3.2-3.5 cm.
*Depth*.—1.0-1.3 cm.
*Total diameter of 'disc'*.—1.2-1.3 cm.
*Receptacle height*.—0.25-0.3 cm.
*Receptacle diameter*.—0.35 cm.

Ray florets:
*Average quantity of florets*.—Average of 36 in 1-2 whorls.
*Color of florets, upper surface*.—RHS 160A ground color heavily overlaid and mottled with RHS 175B to RHS 175C with RHS 178A margins. Color just very faintly fades as it matures.
*Lower surface*.—RHS 160A ground color lightly overlaid and mottled with a muted hue of RHS 175B to RHS 175C with darker margins.
*Length*.—1.7-1.8 cm.
*Width*.—0.45 cm.
*Shape*.—Elliptical.
*Apex shape*.—Slightly emarginated to praemorse, a few are obtuse.
*Margin*.—Entire.
*Texture, upper surface*.—Papillose.
*Lower surface*.—Papillose.

Disc florets:
*Average quantity of florets*.—About 200.
*Color of florets*.—RHS 2C with a RHS 9B apex.
*Length*.—0.45-9.5 cm.
*Width*.—0.1 cm.
*Shape*.—Tubular, elongated.
*Apex shape*.—Acute, 5 pointed.

Phyllaries:
*Quantity*.—Approximately 25.
*Color, upper surface*.—RHS 137C.
*Lower surface*.—Closest to RHS 137A but appears lighter due to hairs.
*Length*.—0.35-0.4 cm.
*Width*.—0.1-0.15 cm.
*Shape*.—Ovate to lanceolate.
*Apex shape*.—Acute.
*Base*.—Fused.
*Margins*.—Entire; papery with RHS 165A edges.
*Texture, upper surface*.—Glabrous.
*Lower surface*.—Bifid T-shaped hairs.

Reproductive organs:
*Found on both florets*.—Yes.
*Pistil*.—1.
*Length*.—0.4-0.45 cm.
*Style color*.—RHS 2C.
*Style length*.—0.3 cm.
*Stigma color*.—RHS 9A.
*Stigma shape*.—Bi-parted.
*Ovary color*.—Not observed.
*Found on only disc florets*.—Yes.
*Stamens*.—4.
*Color of filaments*.—RHS 2D but more translucent looking.

*Length filaments*.—0.2 cm.
*Anther color*.—Closest to RHS 9C.
*Anther length*.—0.1 cm.
*Anther shape*.—Oblong.
*Color of pollen*.—RHS 14B.
*Pollen amount*.—Some.
*Fertility/seed set*.—Has not been observed on this hybrid.
*Disease/pest resistance*.—Has not been observed on this hybrid.

What is claimed is:

1. A new and distinct variety of *Chrysanthemum* plant named 'CIDZ0021' substantially as illustrated and described herein.

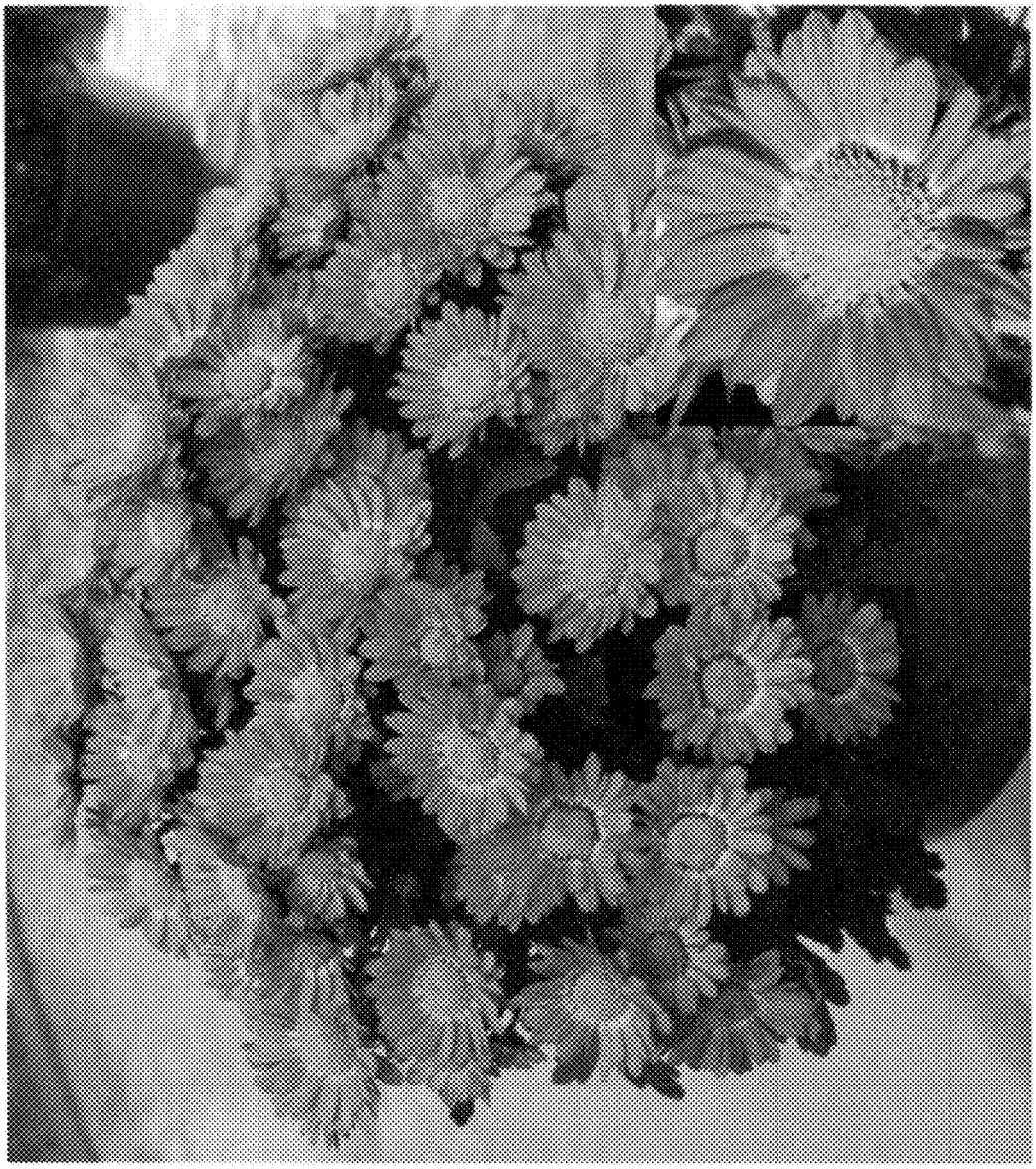

* * * * *